United States Patent [19]

Garcea et al.

[11] Patent Number: 5,213,796
[45] Date of Patent: May 25, 1993

[54] ASSAY FOR POLYOMAVIRUS IN HUMANS AND USES THEREOF

[75] Inventors: Robert L. Garcea, Wellesley; Daniel J. Bergsagel, Arlington, both of Mass.

[73] Assignee: Dana Farber Cancer Institute, Boston, Mass.

[21] Appl. No.: 695,647

[22] Filed: May 6, 1991

[51] Int. Cl.$^5$ .............................................. A61K 39/12
[52] U.S. Cl. ........................................... 424/89; 435/5
[58] Field of Search ................................ 435/5; 424/89

[56] References Cited

PUBLICATIONS

Dubensky et al.-J. of Virology, vol. 50, No. 3, (1984) pp. 779–783.
Shah and Nathanson, Amer. J. of Epid. 103:1–12 (1976).
Small, et al., Proc. Natl. Acad. Sci. 83:8288–8292 (1986).
Walker & Padgett, Polyomavirus & Human Neurol. Diseases, Alan R. Liss, Inc., 99–106 (1983).
Brinster, R. L. et al., Cell 37:367–379 (1984).
Krieg, P., et al., Proc. Natl. Acad. Sci. 78:6446–6450 (1981).
Ellenbogen, R. G., et al. Neurosurgery 25:327–335 (1989).
Arrameas and Ternynck, Immunochemistry 8:1175 (1975).
Jablonski, Anal. Biochem. 148:199 (1985).
Bergsagel, et al., Laboratory Investigation, vol. 64, No. 1, (1991).
Bergsagel, D. J., et al., Clinical Res. vol. 38, No. 2 (1990).
Dialog Information Services, File 351:World Patent Index 81–92, Access. No. 008908671, (MITC) Mitsui Petrochem Ind. KK).
Gernot, Walter, et al., Proc. Natl. Acad. Sci. USA, vol. 86, (Nov. 1989).
Wiekowski, J., et al., Dialog Information Services, file 154:Medline 66–92/May, Access. No. 06138936.
Gibson, P. E., et al., Dialog Information Services, file 154: Medline 66–92/May Access. No. 05813036.
Arthur, R. R., et al., Dialog Information Services, file; 154, Medline 66–92/May, Access. No. 05709274.

*Primary Examiner*—Sam Rosen
*Attorney, Agent, or Firm*—David G. Conlin; Ronald I. Eisenstein

[57] ABSTRACT

Methods for detecting the propensity for an individual to be affected by a polyomavirus are disclosed. The methods include an assay wherein a biological specimen from a female is contacted with at least one probe capable of determining whether the female has been exposed to a polyomavirus. A method for prophylactically treating the female is also described.

13 Claims, No Drawings

ASSAY FOR POLYOMAVIRUS IN HUMANS AND USES THEREOF

The present invention is directed to assays for polyomaviruses, uses of the assays and prophylactic strategies for treatment of women of childbearing years.

Polyomaviruses (sometimes referred to as papovaviruses) are double-stranded DNA viruses, which have been found in a wide variety of species. JC virus (JCV) and BK virus (BKV) are ubiquitous human polyomaviruses that have been associated with specific tumor histologies in rodents. Simian virus 40 (SV40) is a polyomavirus found in monkeys. This virus was also found in the cells used to grow the first polio vaccine [Shah and Nathanson, *Amer. J. of Epid.*, 103.1-12 (1976)]. Approximately 60 to 70% of the adult population is seropositive for each of these viruses. [Small, et al., *Proc. Natl. Acad. Sci.*, 8288-8292 (1986); Walker and Padgett, Polyomaviruses and Human Neurol. Diseases, Alan R. Liss. Inc., pp. 99-106 (1983)].

These viruses can oncogenically transform human and rodent cells in vitro and have induced tumors in newborn hamsters. In addition, BKV and JCV have been found associated with tumors in immunosuppressed patients.

Transgenic mice developing from eggs containing the early region genes from SV40 developed brain tumors within the choroid plexus [Brinster, R. L., et al., *Cell.* 37:367-379 (1984)]. Although researchers have been looking for an association of SV40 with tumors in humans [Krieg, P., et al., *Proc. Natl. Acad. Sci.* 78:6446-6450 (1981)], it has not been found in reproducible studies, which have not been flawed by some type of error in technique or tissue culture contaminant.

Transgenic mice developing eggs containing the early region of JCV or BKV resulted in low reproduction rates and/or development of tumors leading to early deaths. [Small, J., et al., *PNAS* 83, supra].

The choroid plexus is a specialized cell type found in the brain which is responsible for making cerebrospinal fluid. In humans, choroid plexus (CP) tumors occur almost exclusively within the first year of life. This tumor is relatively rare but can have serious consequences. [Ellenbogen, R. G., et al., *Neurosurgery* 25:327-335 (1989)].

It would be desirable if there was a means by which propensity for a tumor, such as CP, could be determined so that development of such a tumor can be carefully tracked so that therapeutic methods can be rapidly instituted. It would also be desirable to have a diagnostic method for this tumor at an early stage, so that therapeutic methods can rapidly be taken.

Further, it would be desirable to have a means to prophylactically treat individuals to minimize and/or prevent the occurrence of tumors caused by polomaviruses.

SUMMARY OF THE INVENTION

We have found that a polyomavirus, an SV40-like virus, is associated with a tumor, CP, in humans and that propensity for the tumor occurs at a prenatal stage. We have developed an assay to detect the propensity for an individual to develop a tumor from a polyomavirus. This comprises contacting a biological specimen from a female with a probe which is capable of binding with a polyomavirus, polyomavirus protein or an antibody to a polyomavirus and determining whether binding has occurred. Preferably the female is tested prior to the onset of pregnancy. Preferably, one uses an probe to the antibody and tests biological fluid. The polyomaviruses tested for are preferably BKV, JCV and SV40, more preferably SV40. Using this assay, it is possible to readily determine whether the tested female is at risk for giving birth to an individual who has or will develop a tumor caused by one of these diseases. If the woman tests seropositive, it is unlikely that she will give birth to an individual having tumors caused by one of these diseases. If the woman is seronegative, then she must be watched during her pregnancy to determine whether or not she becomes exposed to one of these polyomaviruses. If the woman changes from seronegative to seropositive, then the fetus can become infected and subsequently, result in an individual who has a propensity for such a tumor. Thus, fetal testing needs to be carried out and subsequent monitoring should also be performed.

One can prophylactically treat a seronegative woman prior to the onstart of pregnancy by administering a vaccine containing a polyoma antigen. In one embodiment this would be by using capsid protein to SV40, capsid protein to BKV and/or capsid protein to JCV in order to develop antibodies for the virus(es) which the female is seronegative to.

DETAILED DESCRIPTION OF THE INVENTION

There are a wide variety of polyomaviruses in all species from birds to humans. Two human polyomaviruses have been identified BKV and JCV. BKV was intially discovered in the urine of renal transplant patients. JCV was found in association with progressive multifocal leukoencephalopathy (PML), which is a central nervous system degenerative disorder seen in immunocompromised individuals. Although up to 70% of the human population tests seropositive to these viruses, no clinical disease entity has been attributed to their primary infection and pathology attributable to their infection has only been seen in the immunosuppressed. The other polyomaviruses were believed to be species-specific, although it has been possible to express the early T antigen of these viruses in rodents, in particular, in hamsters, where a wide histological variety of tumors have resulted. More recently, by the use of transgenic mice, it has been possible to show that BKV, JCV and SV40 induce tumors and/or a reduction in birth rate.

We have now found polyomaviruses present in human malignancies. These tumors begin developing at an age where the likelihood of the viruses being one of the primary etiological factors is very high.

We have discovered that it is possible to determine a population at risk from polyomavirus, for example, at risk for a malignancy caused by such a virus. We describe herein such individuals as individuals having a propensity to be affected by a polyomavirus. This group arises from individuals whose mother was negative to a polyomavirus, for example, seronegative, prior to that individual's conception but became seropositive during pregnancy.

One would test women of childbearing age to determine whether they have been exposed to a polyomavirus. Preferably, one would test for at least the three polyomaviruses that are known to be found in humans, i.e., BKV, JCV and SV40. Most preferably, one would test for the presence of SV40. However, it would be a simple matter to test for the presence of other polyomaviruses by using probes for polyomaviruses found in other species.

One could use any of a number of assay methods. One would contact the biological sample from the female with at least one probe, which is capable of binding to polyomavirus nucleotides, protein, or an antibody to such protein and determine whether binding occurs. The biological sample can be either a tissue sample or biological fluid. If one uses tissue samples, one preferably uses a nucleotide probe, for example, an RNA or DNA probe, which are well known to the person of ordinary skill in the art. One could use a probe for a conserved region encoding the viral large T-antigen, because this protein has been shown to be the oncogene in some polyomaviruses. One could initially use a probe for a conserved region encoding the viral large T-antigen and if this is found, one would thereafter use oligonucleotide probes, for sequences which distinguish between which virus is, or virus(es), are present. Such probes can be made by the person of ordinary skill in the art. One would preferably use polymerase chain reaction (PCR) and Southern analysis.

More preferably, one would test biological fluid such as blood, serum, plasma, urine, cerebrospinal fluid, supernatant from cell lysate, etc. Preferably, one would test blood, serum or urine. More preferably, one would test serum.

For example, one could test for the presence of protein expressed by or antibodies to any of the above-described polyomaviruses. An antibody or cocktail of antibodies can be used, for example, to test for the protein or in a competiton assay. For example, one could use a monoclonal antibody to a polyoma large T-antigen. The particular antibody can readily be determined by the person of ordinary skill in the art. For example, monoclonal antibodies to SV40 large T-antigen are well known in the art and include those deposited with the American Type Culture Collection (ATCC), such as TIB115, TIB117 and TIB230. Antibodies to other polyomaviruses are well known to the person of ordinary skill in the art. Preferably, one would use a cocktail containing antibodies to a wide range of polyomaviruses, preferably, including JCV, BKV and SV40.

More preferably, one would test for the presence of antibodies to the viruses. Such a test can readily be designed by the skilled artisan based upon the present disclosure. For example, one method would be to use proteins to the polyomavirus, such as capsid protein, preferably purified virus capsid protein, in, e.g., an ELISA, and test for maternal antibodies. Another method would be to use antibodies against, for example, the capsid protein in a competition assay for maternal antibodies. Other viral proteins such as the large T antigen can also be used as a target, but the capsid protein is preferred.

If a female tests positive to the presence of a virus, then it is extremely unlikely that the virus will cross the placenta and infect the fetus. However, if a female tests negative, then the female needs to be monitored during her pregnancy to determine whether or not she become infected. This can be done at regular intervals, such as a monthly schedule. If, during the course of pregnancy, the woman does not become infected, the fetus will not become infected either. However, if a woman does become infected during pregnancy, then the fetus is at risk and must be tested to determine whether or not it becomes infected.

This test can be done on women at any time. However, since exposure to these polyomaviruses occur over time, it is preferable that it not be done until a woman reaches childbearing age. Preferably, the individual is at least about 16 years old before tested in this assay. Since a female could become infected after conception but prior to being tested, it is preferable to do this test prior to becoming pregnant. However, even if this is not done, it is still useful to be screened early in pregnancy to see if there is a subsequent change.

Choroid plexus tumors occur in humans almost exclusively within the first year of life. However, this tumor is relatively rare and represents only about 3% of all pediatric brain tumors. One-half are diagnosed before age 1 and 80% by age 5. They are slow growing tumors and their pathology varies. However, the earlier it is possible to discover the tumor, the greater the treatment choices. Because of its rarity, formalin-fixed, paraffin-embedded tissue sections of CP neoplasms from the archives of the Children's Hospital, Boston, Mass., Pathology Department were examined. The polymerase chain reaction technique (PCR) was used to amplify a specific segment of the viral genome. The initial investigation was whether BKV and/or JCV might be present in these tumors. Specimens were examined for the presence of T-antigen sequences for both BKV and JCV. Instead of finding BKV or JCV, we surprisingly found that there was a DNA sequence present which corresponds to an SV40-like virus. As used herein, the term "SV40-like" virus includes the SV40 virus, a fragment of the SV40 virus that retains SV40 properties when tested in vitro, a virus that has a similar genomic organization to SV40 with 2 early and 3 late proteins, and a virus capsid which is non-envelope of T-7 symmetry comprised of 72 capsomeres. As the term is used herein viruses with changes in the promoter region are considered SV40-like. Preferably, the SV40-like virus corresponds to at least 80% of the nucleotide sequence of the SV40 virus encoding the large T antigen, more preferably, it corresponds to at least about 85% of such nucleotide sequence and still more preferably, it corresponds to at least about 90% of such nucleotide sequence.

The correlation between SV40 being present in these tumors, indicates that this polyomavirus is one of the primary etiological factors in the development of the malignancy. As aforesaid, these tumors are generally found in very young infants and are often present at birth. We found a polyomavirus present in a tumor found in a 3 day old. Thus, if the sequences were introduced by infection, the event must be maternal or perinatal. However, seropositivity does not occur until approximately 4-5 years. While there is evidence for transplacental transmission of polyomavirus in mice, previously infected mothers do not pass virus to their offsprings. Thus, we conclude that if a female has not been infected and is negative for the presence of a polyomavirus, but becomes infected during pregnancy then the fetus is at risk for becoming infected. We believe this can result in various malignancies resulting in tumors, and even death of the fetus, which could manifest itself as a miscarriage. If she gives birth, the resulting individual has a propensity to be affected by the polyomavirus. For example, having or developing a tumor from the polyomavirus. One tumor is CP tumor.

We have also found SV40 present in a more common brain tumor, ependymomas, which also occur early in life. More recently we have found SV40 present in osteogenic sarcomas, a bone tumor that develops during the adolescent growth surge. However, these polyomaviruses can be associated with other tumors and other pathological states and the resultant individual born to a female who went from negative to positive during pregnancy is at risk to develop such other diseases and malignancies and should be carefully monitored.

In accordance with this invention, a probe or cocktail of probes, e.g. protein probes, antibody probes or nucleotide probes, can be used for detection. The probes, e.g. proteins or antibodies, can be labelled directly with a reporter or indirectly with a member of a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label proteins such as capsid protein and antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; bitoin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfdhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, protein, detectably-labelled antibodies, or detectably-labelled member of the specific binding pair is coupled to a reporter which can be a radioactive isotope, enzyme, fluorogenic, chemiluminescent or electrochemical materials. Two commonly used radioactive isotopes are $^{125}I$ and $^3H$. Standard radioactive isotopic labeling procedures include the chloramine T, lactoperoxidase and Bolton-Hunter methods for $^{125}I$ and reduction methylation for $^3H$.

Enzymes suitable for use in this invention include, but are not limited to, horseradish peroxidase, alkaline phosphatase, $\beta$-galactosidase, glucose oxidase, luciferase, $\beta$-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, *Immunochemistry* 8:871 (1971), Avrameas and Ternynck, *Immunochemistry* 8:1175 (1975), Ishikawa et al., *J. Immunoassay* 4 (3):209-327 (1983) and Jablonski, *Anal. Biochem.* 148:199 (1985), which are incorporated by reference.

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is an assay in which the capture reagent e.g. coat protein or inactivated virus has been immobilized, using conventional techniques, on the surface of the support in an ELISA-type assay. Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

It is possible to prophylactically treat a female who has not been exposed to a polyomavirus, and is seronegative, prior to becoming pregnant to take such a female out of the risk group. Accordingly, it is preferable that the above-described test be performed on a woman prior to a decision to become pregnant. If a female, who is not pregnant, tests negative for one of these viruses, it is possible to raise antibodies by vaccination. Vaccination against the particular virus that the individual tests negative against can be done by a variety of techniques. Although clinical disease entities have not been found in healthy adults, and the virus can be considered relatively benign, thereby permitting exposure to attenuated whole virus, it is more preferable to inject only a portion of the viruses, for example, its coat protein. Such a vaccine can readily be made by the person of ordinary skill in the art, for example, using a benign virus such as a pox virus, for example, vaccinia virus, as a vector and inserting a capsid protein for one of the polyomaviruses into this viral vector. One could express coat protein for one of these viruses in a host cell. The host cell can be any of a wide range of cell lines, for example, CHO, *E. coli*, *B. subtillis*. etc. Preferably, one would use *E. coli*. Thereafter, one would purify the coat protein by standard techniques and inject a purified preparation of the coat protein. Preferably, this would be in a pharmacologically inert carrier.

The preparation can be delivered by any of a number of means. For example, it either can be administered by parenteral injection (intramuscular (i.m.), intraperitoneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The preparation will preferably be formulated in a unit dosage form.

For example, solid dose forms that can be used for oral administration include capsules, tablets, pills, powders and granules. In such solid dose forms, the active ingredient, i.e., capsid protein, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the viral protein. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

Thereafter, the female can be tested to determine whether or not she has developed antibodies and thus become seropositive to this virus. Such a female has now prophylactically treated to avoid risk of infection.

The present invention is further illustrated by the following examples. These examples are provided to aid in the understanding of the invention and are not to be construed as a limitation thereof.

METHODS

Tissue

Fresh tumor tissue came from the Children's Hospital Boston, Mass. and St. Jude's Children's Research Hospital. It was frozen in liquid nitrogen at the time of surgery and kept at −70° C. until processed. Formalin-fixed, paraffin-embedded tissue came from the Children's Hospital Boston and from the University of Texas. New sections were prepared from each tumor specimen. Lymphocytes were separated from whole blood by centrifugation through ficoll. Neuroblastoma DNA was kindly provided by Bruce Korf, Children's Hospital, Boston. The whole blood came from healthy volunteer blood donors at Children's Hospital, Boston, Mass.

DNA Extraction

Fresh Tissue and Lymphocytes

Fresh tissue was minced with a sterile scalpel blade as it thawed from −70° C. It was suspended in PCR buffer ( 50 mM KCI, 10 mM Tris-HCl pH 8.3, 2.5 mM MgCl$_2$, 0.1 mG/ml gelatin ) with 0.5% Tween 20 and 60 µG/mL proteinase K [Kawasaki, E.S., *A Guide to Methods and Applications*, Innis, Gelfand, Sninsky and White, ed.. Acad. Press, San Diego (1990).], and incubated at 55° C. overnight with shaking. Following phenol/chloroform extraction DNA was precipitated with ammonium acetate and ethanol. After drying it was resuspended in water.

PARAFFIN EMBEDDED TISSUE

One to 5 section 5–10 µM thick on glass slides were covered with xylenes, decanted, repeated once, then covered with absolute ethanol, decanted, repeated once, then allowed to air dry. The sections were scraped off the slide with a fresh, flamed razor blade and placed in a sterile, siliconized 0.6 mL tube (Robbins, Mountain View, Calif.). Two-hundred µL PCR buffer with 0.5% Tween 20 and 60 µG/mL of Proteinase K (Boehringer) was added and the samples were incubated at 55° C. with shaking until completely digested (12 to 72 hours). After phenol/chloroform extraction the DNA was precipitated with sodium acetate or ammonium acetate and ethanol, washed with 70% ethanol, and dried under vacuum. Fifty µL of water was added and the specimens heated to 65° C. for three minutes then vortexed. One-half to 5 µL of this were used for subsequent PCR analysis.

WHOLE BLOOD

One-half mL of whole blood was lysed in 0.32 M sucrose, 10 mM Tris-HCl (pH 7.5), 5mM MgCl$_2$, 1% Triton x-100 and spun briefly in a microcentrifuge to pellet nuclei. This extraction was repeated twice more then the pellet suspended in 0.5 mL of PCR buffer with 0.5% Tween 20 and 60 mg/mL of Proteinase K and incubated for one hour at 55° C. then 10 minutes at 100° C. [Higushi, R., *Amplifications* 1(2):1-3, (1989)].

PCR Strategy

All oligos are homologous to regions of the large T-antigens of BKV, JCV, and SV40. Oligos PYV.for and PYV.rev match perfectly to sequences in both BKV and JCV, and amplify 182 and 179 base pair regions respectively. PYV.for has 3 mismatches and PYV.rev has 2 mismatches with the homologous region of SV40, and span a 174 base pair region. BK.for$_2$ and BK.rev amplify a 103 base pair region from BKV only. JC.for$_2$ and JC.rev amplify a 102 base pair region from JCV only. SV.for$_2$ and Sv.rev amplify a 574 base pair region from SV40 only which includes the single intron. SV.for$_3$ and SV.rev amplify a 105 base pair region of SV40 only.

AG$_1$ and AG$_2$ amplify a 396 base pair region of the A gamma globin and G gamma globin genes in humans.

The sequenes (5' to 3') for the oligonucleotides used were: PYV.for TAGGTGCCAACCTATGGAACAGA, PYV.rev GGAAGTCTTTAGGGTCTTCTACC, BK.probe GAGAATCTGCTGTTGCTTCTT, JC.probe GTTGGGATCCTGTGTTTTCAT, SV.for2 CTTTGGAGGCTTCTGGGATGCAACT, SV.for3 TGAGGCTACTGCTGACTCTCAACA, SV.probe ATGTTGAGAGTCAGCAGTAGCC, SV.rev GCATGACTCAAAAAACTTAGCAATTCTG, AG1 ACACTCGCTTCTGGAACGTCTGAG, AG2 AAACGGCTGACAAAAGAAGTCCT, AG3 AAACTAGCTAAAGGGAAG.

| | PCR Amplification of DNA |
|---|---|
| Buffers: | *Thermus acquaticus* polymerase - 50 mM KCl, 10 mM Tris HCl pH 8.3, 1.5 mM MgCl$_2$, .1 mG/mL gelatin. *Thermus flavus* polymerase - 50 mM Tris HCl pH 9.0, 20 mM ammonium acetate, 1.5 mM MgCl$_2$ |
| Nucleotides: | 200 μM (Boehringer) |
| Oligos: | 1 μM each except AG$_1$ and AG$_2$ which were used at .33 μM. |
| Enzymes: | Taq polymerase (Amplitaq, Perkin-Elmer Cetus) or *T. flavus* polymerase (Replinase, Dupont) 2.5 units/100 μL reaction. |
| Controls: | BK - BK containing plasmid (pBKpML, provided by M. M. Pater, Memorial University, Newfoundland). JC-DNA extracted from a single reaction of PML brain diluted 10,000 fold (provided by J. Morris, Brigham amd Women's Hospital, Boston, Massachusetts). SV40 - cosmid containing SV40 large T antigen cDNA (provided by P. Bradley, Dana-Farber Cancer Institute, Boston, Massachusetts). Negative control - multiple tubes without added DNA were included in every run. |

Thermocyling was performed by first heating to 94° C. for 3 minutes, the samples then underwent 45 to 60 cycles of 94° C. for one minute, 52° C. for one minute, 72°C. for one minute (except for SV.for2/SV.rev, for which the respective parameters were 94° C., one minute, 57° C., two minutes, 72° C., three minutes).

Southern Blot Analysis and Detection with Oligonucleotide Probes

Ten μL of the PCR product were separated on a 3% NuSieve/1% SeaKem/1X TBE agarose gel, electrophoresed in TBE, strained with ethidium bromide and photographed under UV light. The gel was denatured in 0.4 N NaOH, 0.6M NaCl, neutralized in 0.5 M Tris - HCl pH 7.5, 1.5 M NaCL, then transferred to a nylon membrane (Duralon UV, Stratagene). The filters were pre-hybridized in 5X SSC, 5X Denhardt's solution, 20 mM NaH$_2$PO$_4$, 500 mg/mL salmon sperm DNA at 42° C. for two hours, hybridized in 5X SSC, 1% SDS, 20mM NaH$_2$PO$_4$, 500 mg/mL salmon sperm DNA with $10^6$ CPM/mL of end-labelled oligonucleotide probe at 42° C. overnight, washed for 5 minutes in 2X SSC, 1% SDS 3 times at room temperature and once at 42° C., and exposed to film for 12 to 120 hours.

Restriction Enzyme Digestion of PCR Products

The appropriate sized band from the first PCR reaction was cut out of a 4% NuSieve gel. melted at 70° C. for 10 minutes then diluted to 1 mL with water and 10 μL used in a second PCR reaction with the same oligos for 30 cycles. The product was extracted with phenol/chloroform, ethanol precipitated and resuspended in 10 μL water. One μL was digested in appropriate buffer with BstX I and Fok I and the mixture electrophoresed on a 10% acrylamide gel. For sequencing the second PCR product was purified on a Centricon 100 column (Amicon) to remove residual primers, and then used for dideoxy sequencing (Sequenase, United States Biochemicals).

The results are set forth below.

| | SEX | AGE | TUMOR TYPE[a] | FRESH/PARAFFIN | VIRUS |
|---|---|---|---|---|---|
| 1. | M | 3 days | CP tumor (malignant) | paraffin | SV40 |
| 2. | F | 16 yrs | CP papilloma (low grade) | paraffin | SV40 |
| 3. | M | 8 yrs | CP papilloma | paraffin | INADEQ |
| 4. | M | 11 mos | CP papilloma | praffin | SV40 |
| 5. | M | 11 yrs | CP papilloma (benign) | paraffin | INADEQ |
| 6. | F | 1 yr | CP papilloma (malignant) | paraffin | INADEQ |
| 7. | F | 8 mos | CP papilloma (hydrocephalus in utero) | paraffin | SV40* |
| 8. | F | 9 mos | CP papilloma (repeat bioposy of 7) | paraffin | SV40 |
| 9. | M | 1 mo | CP papilloma (mucus secreting) | paraffin | SV40 |
| 10. | M | 3 mos | CP tumor (malignant) | paraffin fresh | NEG SV40 |
| 11. | M | 2 yrs | CP carcinoma | paraffin | SV40 |
| 12. | M | 2 yrs | CP carcinoma (repeat biopsy of 11) | paraffin | SV40 |
| 13. | M | 4 yrs | CP carcinoma | paraffin | NEG |

-continued

|     | SEX | AGE | | | |
|-----|-----|-----|---|---|---|
|     |     |     |   | fresh | NEG |
| 14. | F | 11 mos | CP carcinoma | paraffin | SV40* |
| 15. | M | 23 mos | CP neoplasm | paraffin | SV40 |
| 16. | M | 2 mos | CP carcinoma (from cerebellum) | paraffin | SV40 |
| 17. | M | 9 mos | CP carcinoma (repeat biopsy of 16) | paraffin | SV40* |
| 18. | M | 8 yrs | CP carcinoma | fresh | SV40 |
| 19. | M | 5 wks | CP carcinoma | paraffin | SV40 |
| 20. | M |  | CP carcinoma (repeat biopsy of 19) | fresh | SV40 |
| 21. |  |  | CP tumor (C90-81) | paraffin | SV40 |
| 22. |  |  | CP tumor (C90-82) | paraffin | NEG |
| 23. | M |  | CP papilloma (R.M.) | fresh | NEG |
| 24. | M |  | CP carcinoma (C.G.) | fresh | SV40 |
| 25. | F | 3 mos | CP papilloma (B.G.G.) | fresh | SV40 |

SUMMARY:
A. 3 paraffin samples were determined to be inadequate (as judged by ability to amplify the globin control), 3 paraffin samples negative (one shown to be positive from fresh tissue), 16 positive (12 positive individuals, 4 repeat positive biopsies), three positive sequenced and shown to be SV40*.
B. 3 fresh specimens positive, 2 negative.
al., Neurosurgery, 25, supra.

*Tumors were classified based upon the system of Ellenbogen, R. G., et

| | | EPENDYMOMAS | | |
|---|---|---|---|---|
| | SEX | AGE | TUMOR TYPE | FRESH/PARAFFIN | VIRUS |
| 1. |  |  | Ependymoma | paraffin | SV40 |
| 2. | F | 2 yrs | Ependymoma | paraffin | SV40 |
| 3. | F | 9 yrs | Ependymoma | paraffin | SV40 |
| 4. |  |  | Ependymoma | paraffin | NEG |
| 5. | M | 8 mos | Ependymoma | paraffin | SV40 |
| 6. | M | 3 yrs | Ependymoma | paraffin | SV40 |
| 7. | F | 17 yrs | Ependymoma | paraffin | SV40 |
| 8. | M | 8 yrs | Ependymoma | paraffin | SV40 |
| 9. |  |  | Ependymoma | fresh | NEG |
| 10. |  |  | Ependymoma | fresh | SV40 |

SUMMARY:
A. PARAFFIN: 1 Sample Negative, 7 Positive
B. FRESH: 1 Fresh Specimen Positive, 1 Negative
C. TOTAL: 8 of 10 patients Positive for SV40.

These results indicate that SV40 is an etiological agent for these neoplasms. The results also indicate, as aforesaid, that the disease occurred in the prenatal state. Accordingly, these results indicate that polyomaviruses in the neonatal state can cause tumors.

The above-described procedure was used with tissue samples from the following tumors: osteosarcoma, breast, brain, adrenal, soft tissue sarcoma, Ewing's sarcoma and ovarian. Both somatic tissues and tumor tissue from individuals having familial cancer syndrome were examined. The results are set forth in the table below.

| Tumor | DNA Source$_1$ | SV. for$_3$/Sv. rev | | | SV. for$_2$/Sv. rev | | |
|---|---|---|---|---|---|---|---|
| | | + | − | total | +$^2$ | − | total |
| Osteosarcoma | Somatic | 16 | 0 | 16 | 7 | 8 | 15 |
| | Tumor | 16 | 0 | 16 | 6 | 10 | 16 |
| | Unknown | 2 | 0 | 2 | 0 | 2 | 2 |
| Breast | Somatic | 10 | 1 | 11 | 6 | 4 | 10 |
| | Tumor | 1 | 0 | 1 | 1 | 0 | 1 |
| "Tumor" | Somatic | 2 | 0 | 2 | 1 | 1 | 2 |
| | Tumor | 4 | 0 | 4 | 3 | 0 | 3 |
| Brain | Somatic | 2 | 1 | 3 | 0 | 3 | 3 |
| Adrenal | Somatic | 0 | 1 | 1 | 1 | 0 | 1 |
| | Tumor | 1 | 0 | 1 | 0 | 1 | 1 |
| Osteosarcoma and Breast | Somatic | 2 | 0 | 2 | 0 | 2 | 2 |
| Osteosarcoma and Soft Tissue Sarcoma | Somatic | 1 | 0 | 1 | 1 | 0 | 1 |
| Osteosarcoma and Ewing's Sarcoma | Somatic | 1 | 0 | 1 | 1 | 0 | 1 |
| Soft Tissue Sarcoma | Somatic | 1 | 0 | 1 | 1 | 0 | 1 |
| Ovarian | Somatic | 0 | 1 | 1 | 1 | 0 | 1 |

| Tumor | DNA Source[1] | SV. for₃/Sv. rev + | - | total | SV. for₂/Sv. rev +[2] | - | total |
|---|---|---|---|---|---|---|---|
| Subtotal | | 59 | 4 | 63 | 29 | 31 | 60 |
| None | Somatic | 3 | 5 | 8 | 1 | 4 | 5 |
| | Unknown | 4 | 0 | 4 | 0 | 4 | 4 |
| Unknown | Unknown | 29 | 24 | 53 | 5 | 48 | 53 |
| Unknown | Somatic | 13 | 8 | 21 | 3 | 4 | 7 |
| Subtotal | | 49 | 37 | 86 | 9 | 60 | 69 |
| TOTALS | | 108 | 41 | 149 | 38 | 91 | 129 |

[1]Somatic DNA source was blood, fibroblast cell line or lymphoycte cell line.
[2]Viral 574 bp amplified These results show a correlation between the presence of a polyomavirus and both breast tumors and osteosarcoma.

It is evident that those skilled in the art, given the benefit of the foregoing disclosure, may make numerous other uses and modifications thereof and departures from the specific embodiments described herein without departing from the inventive concepts, and the present invention is to be limited solely by the scope and spirit of the appended claims.

We claim:

1. A method for prophylactically treating a female to minimize the female's chance of infecting a fetus with a polyomavirus, which comprises:
   (a) contacting a biological specimen from the female with at least one probe which is capable of binding with a polyomavirus, a polyomavirus protein, or an antibody to a polyomavirus;
   (b) determining whether binding has occurred;
   (c) if binding has not occurred, vaccinating the female with a vaccine containing an antigenic portion of the polyomavirus.

2. The method of claim 1, wherein the biological specimen tested is biological fluid.

3. The method of claim 2, where the biological fluid is selected from the group consisting of blood, serum, plasma, urine, cerebrospinal fluid, and supernatant from cell lysate.

4. The method of claim 3, wherein the probe binds with an antibody to a polyomavirus.

5. The method of claim 1, wherein the polyomavirus is selected from the group consisting of JC virus, BK virus and Simian virus 40-like virus.

6. The method of claim 5, wherein the virus is Simian virus 40-like virus.

7. The method of claim 1, wherein the antigenic portion of the polyomavirus is the capsid protein.

8. The method of claim 7, wherein the capsid protein is selected from the capsid proteins of JC virus, BK virus and Simian virus 40-like virus.

9. The method of claim 9, wherein the capsid protein is Simian virus 40 protein.

10. The method of claim 1, wherein a cocktail of probes to polyomaviruses are used.

11. The method of claim 4, wherein the probe is a polyomavirus protein.

12. The method of claim 11, wherein the probe is a polyomavirus coat protein.

13. The method of claim 11, wherein the probe is used in ELISA.

* * * * *